(12) United States Patent
Farazi et al.

(10) Patent No.: US 8,165,664 B1
(45) Date of Patent: Apr. 24, 2012

(54) SYSTEMS AND METHODS FOR INCREASED SPECIFICITY IN DIAGNOSTICS

(75) Inventors: Taraneh Ghaffari Farazi, San Jose, CA (US); Rupinder Bharmi, Stevenson Ranch, CA (US); Brian Jeffrey Wenzel, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1206 days.

(21) Appl. No.: 11/928,233

(22) Filed: Oct. 30, 2007

(51) Int. Cl.
*A61B 5/0402* (2006.01)
(52) U.S. Cl. ........................................ 600/509
(58) Field of Classification Search .......... 600/301, 600/508–510, 516–517
See application file for complete search history.

(56) References Cited

U.S. PATENT DOCUMENTS

| | | |
|---|---|---|
| 5,560,368 A | 10/1996 | Berger |
| 6,821,256 B2 | 11/2004 | Ackerman et al. |
| 7,174,204 B2 | 2/2007 | Hadley et al. |
| 2002/0143265 A1 | 10/2002 | Ackerman et al. |
| 2005/0010124 A1 | 1/2005 | Couderc et al. |
| 2006/0167365 A1 | 7/2006 | Bharmi |

OTHER PUBLICATIONS

Valverde et al. "Beat to Beat Repolarization Variability Measured by T Wave Spectral Variance Index in Chronic Infarcted Animals," A.N.E., vol. 7, No. 4 (Oct. 2002).

*Primary Examiner* — Carl H Layno
*Assistant Examiner* — Jessica Sarcione
(74) *Attorney, Agent, or Firm* — Steven M Mitchell

(57) ABSTRACT

Specific embodiments provided herein relate to diagnosing, with improved specificity, occurrences of episodes relating to disorders that are known to affect T-wave morphology. One or more propensity metric is obtained, each of which is indicative of a patient's propensity for a specific disorder that is known to affect T-wave morphology. T-wave variability is monitored. Additionally, there is monitoring for a specific change in T-wave morphology that is known to be indicative of episodes relating to a disorder. When the specific change in T-wave morphology is detected, a diagnosis is determined for detecting the specific change in T-wave morphology, taking into account the propensity metric(s) and the T-wave variability.

21 Claims, 9 Drawing Sheets

SYSTEMS AND METHODS FOR INCREASED SPECIFICITY IN DIAGNOSTICS

FIELD OF THE INVENTION

Embodiments of the present invention relate to systems and methods for diagnosing, with improved specificity, occurrences of episodes relating to disorders that are known to affect T-wave morphology. Exemplary disorders include, but are not limited to, myocardial ischemia, kidney dysfunction and coronary artery disease.

BACKGROUND

Simple parameter extraction of an IEGM can be a very useful tool in a variety of diagnostic features. Many algorithms in implantable or external medical devices are being or have been developed for diagnosing various conditions based on information extracted from the IEGM and various segments within a cardiac cycle. Many of these algorithms, such as ischemia detection, electrolyte imbalance, hypo- and hyper-glycemia, etc., are based on parameters extracted from the repolarization segment (the T-wave) of the IEGM. Because of the sensitivity of the T-wave to changes in $O_2$, electrolytes, glucose, etc., such algorithms generally have a high sensitivity but lack good specificity. It would be beneficial if the specificity of such algorithms can be increased. More generally, it would be beneficial to increases the specificity of diagnostics based at least in part on measures of T-wave metrics of an IEGM.

SUMMARY

Some embodiments of the present invention relate to systems and methods for diagnosing, with improved specificity, occurrences of episodes relating to disorders that are known to affect T-wave morphology. Other embodiments use similar techniques to monitor patients overtime to facilitate early detection of disease onset, to track the patient's cardiac health and/or to track the patient's general well being.

In accordance with certain embodiments of the present invention, one or more propensity metric(s), each of which is indicative of a patient's propensity for a disorder, is/are obtained, where such disorder(s) is/are known to affect T-wave morphology.

In accordance with certain embodiments of the present invention, a patient's T-wave variability is monitored. This can include measuring one or more T-wave metric of T-waves in one or more IEGM and/or ECG obtained for the patient, and determining the T-wave variability based on the measured T-wave metrics. T-waves are the repolarization segments of a cardiac cycle of an ECG or an IEGM. Such an IEGM can be a ventricular IEGM or an atrial IEGM, or both. Exemplary T-wave metrics, upon which T-wave variability can be based, include peak-to-peak amplitude of T-wave, maximum amplitude of T-wave, location of maximum amplitude of T-wave, minimum amplitude of T-wave, location of minimum amplitude of T-wave, area under T-wave, slope of T-wave, T-wave centroid, QT interval, corrected QT interval, amplitude of ST segment, QT max-QT end, T-wave frequency content and T-wave frequency spread.

Additionally, a specific change in T-wave morphology is monitored for, where the specific change is known to be indicative of episodes relating to a disorder. In accordance with certain embodiments, when the specific change in T-wave morphology is detected, a diagnosis for detecting the specific change in T-wave morphology is determined, taking into account the propensity metric(s) and the T-wave variability. In accordance with certain embodiments, a level of confidence can be determined for the diagnosis. For example, a diagnosis can have a high, medium or low level of confidence. More or less confidence levels are also possible.

Exemplary disorders, episodes of which can be diagnosed with improve specificity using embodiments of the present invention, include, but are not limited to, diabetes, myocardial ischemia, kidney dysfunction and coronary artery disease. For example, embodiments of the present invention can be used to detect hypoglycemic episodes and hyperglycemic episodes with improved specificity. Embodiments of the present invention can also be used to detect ischemic episodes with improved specificity. Additionally, embodiments of the present invention can be used to detect hyperkalemic episodes and hypokalemic episodes with improved specificity, as well as episodes of angina with improved specificity. Other exemplary disorders that can be detected using embodiment of the present invention include heart failure (HF), myocardial inhomogeneity, and electrolytic imbalances, but are not limited thereto.

In accordance with certain embodiments, measures of T-wave variability can be used to track the general well being and/or the cardiac health of a patient. Additionally, or alternatively, monitored T-wave variability can be used to trigger an alarm, and/or to trigger the monitoring for a specific change in T-wave morphology that is known to be indicative of episodes relating to a disorder. Information indicative of the T-wave variability can be stored, so that changes in the T-wave variability over time can be determined based on the stored information. Increases in T-wave variability can be interpreted as being indicative of a worsening of a patient's cardiac health (and/or general well being), and decreases in T-wave variability can be interpreted as being indicative of an improvement of the patient's cardiac health (and/or general well being).

This description is not intended to be a complete description of, or limit the scope of, the invention. Other features, aspects, and objects of the invention can be obtained from a review of the specification, the figures, and the claims.

DETAILED DESCRIPTION

Figure 1A:
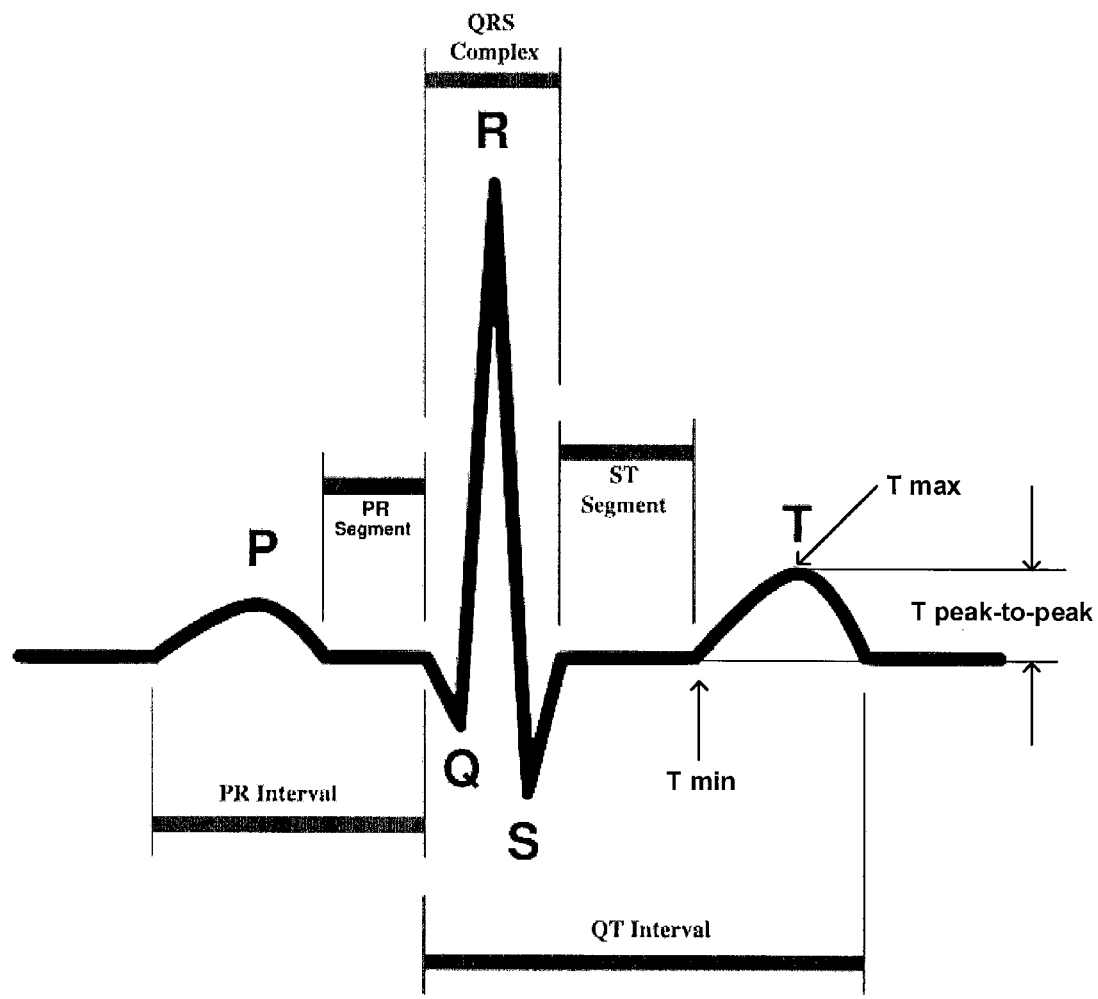
FIG. 1A illustrates an exemplary portion of an ECG signal, including some of its morphologic features.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

A comorbidity is a disorder or disease, in additional to a primary disease or disorder. As used herein, the terms "disorder" and "disease" are used interchangeably. Exemplary disorders include, but are not limited to, diabetes, myocardial ischemia, kidney dysfunction and coronary artery disease. Any one of these exemplary disorders can be a patient's primary disease, with one or more of the other disorders being comobidities. Other primary disorders and comorbid disorders are also possible, and likely.

Disorders can result in episodes relating to the disorder, also referred to as disorder events. For example, when diabetes is a disorder of a patient, that patient may experience episodes relating to the disorder, such as hypoglycemic episodes. For another example, when a patient has myocardial ischemia, that patient may experience ischemic episodes. In another example, when a patient has kidney dysfunction, that patient may experience hyperkalemic episodes and/or hypokalemic episodes. For a last example, when a patient has coronary artery disease, that patient may experience episodes of angina.

Episodes relating to each of the above mentioned disorders affect the morphology of an intracardiac electrogram (IEGM) and an electrocardiogram (ECG), which are detectable/obtainable signals indicative of the electrical activity of a patient's heart. More specifically, episodes relating to the above mentioned disorders typically affect the repolarization segments of such signals, i.e., the T-wave morphology. Even more specifically, for each of the above disorders, there is a specific change in T-wave morphology that is known to be indicative of episodes relating to the disorder. For example, QT interval prolongation is known to be indicative of a hypoglycemic episode. Additionally, increases in corrected QT interval dispersion are known to be indicative of a hyperglycemic episode. For another example, ST segment deviation is known to be indicative of an ischemic episode. Additionally, ST segment elevation is known to be indicative of a hyperkalemic episode, and ST segment depression is known to be indicative of a hypokalemic episode. ST segment depression is also known to be indicative of episodes of angina.

Because it is known how various disorders can affect T-wave morphology, many detection algorithms rely on measures of T-wave morphology to detect episodes of a disorder (where the disorder can be the primary disorder or a comorbidity). For example, an ischemic episode detection algorithm can monitor for ST segment deviations. Such algorithms may have a relatively high sensitivity. However, since T-wave morphology can be affected by many other factors, such as $O_2$, electrolytes, glucose, etc., as well as episodes of other disorders (e.g., comorbidities), these detection algorithms often have lower than desired specificities.

As used herein, sensitivity refers to the likelihood that an episode relating to a disorder (e.g., an ischemic episode) will actually be characterized as the episode relating to the disorder; and specificity refers to the likelihood that only the episodes relating to the disorder (as opposed to episodes relating to another disorder) will actually be characterized as episodes relating the disorder. For example, an ischemia detection algorithm can have a 100% sensitivity and an 80% specificity if it always characterizes ischemic episodes as ischemic episodes, but also characterizes some hyperkalemic episodes as ischemic episodes. For another example, an ischemic detection algorithm can have an 80% sensitivity and a 100% specificity if it never mischaracterizes hyperkalemic or other episodes as ischemic episodes, but misses detecting some episodes of ischemia.

Specific embodiments of the present invention relate to systems and methods for diagnosing, with improved specificity, occurrences of episodes relating to a disorder that is known to affect T-wave morphology. Such embodiments keep track of the variability of one or more T-wave metric over time. Additionally, such embodiments take into account the patient's propensity for the specific disorder and/or the patient's propensity for another disorder that is also known to affect T-wave morphology.

Figure 1B:
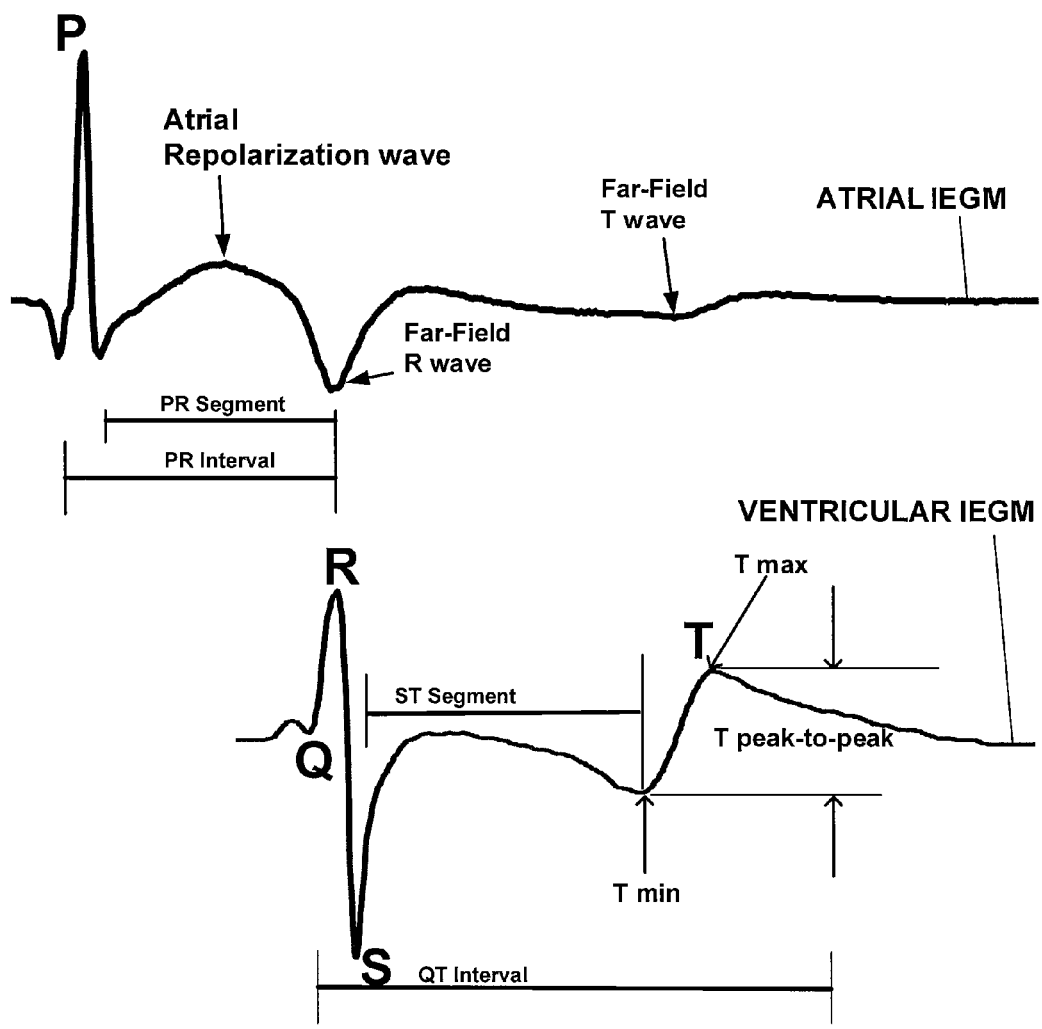
FIG. 1B illustrates exemplary portions of an atrial IEGM and a ventricular IEGM, including some of their morphological features.

FIG. 1A illustrates an exemplary portion of an ECG signal, including some of its morphologic features. FIG. 1B illustrates exemplary portions of an atrial IEGM and a ventricular IEGM, including some of their morphological features. Included in the illustrations is a P-wave, a Q-, R- and S-wave (which make up a QRS complex) and a T-wave. Also shown are some of the various metrics of the signal that can be measured, including PR interval, PR segment, ST segment, QT interval, maximum amplitude of T-wave (Tmax), minimum amplitude of T-wave (Tmin), and peak-to-peak amplitude of T-wave (T peak-to-peak). As can be appreciated, many of these metrics relate to the T-wave morphology. Thus, many of these metrics may be affected by disorders that are known to affect T-wave morphology. Additional metrics of T-wave morphology include, but are not limited to, location of maximum amplitude of T-wave, location of minimum amplitude of T-wave, area under T-wave, slope of T-wave, T-wave amplitude dispersion, T-wave centroid, QT interval, QT interval dispersion, corrected QT interval dispersion, amplitude of ST segment, T-wave frequency content, and T-wave frequency spread. As will be appreciated from the following discussion, one or more of these metrics may be affected by specific disorders, and thus, can be used to attempt to detect episodes relating to specific disorders.

Figure 2A:
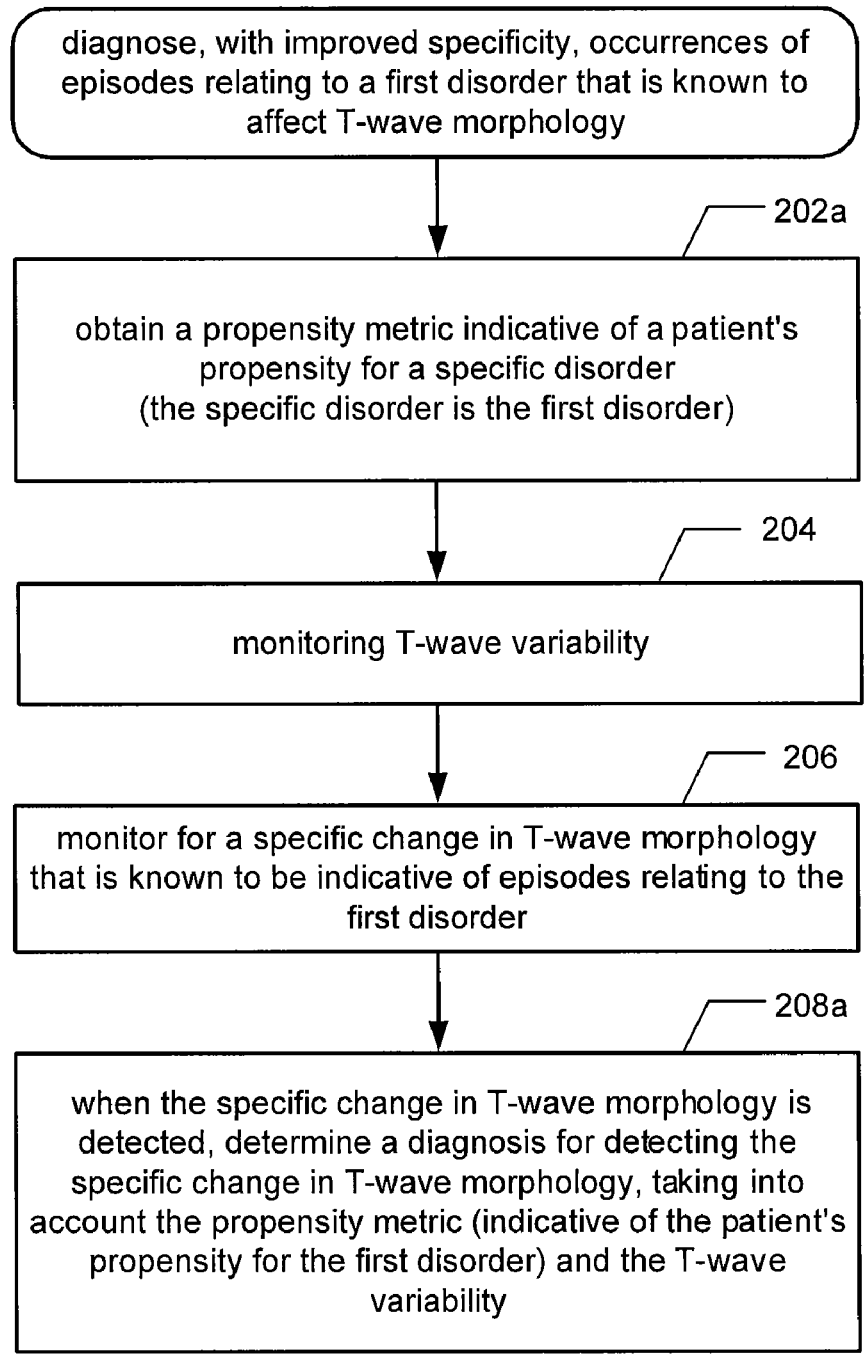
FIGS. 2A-2C are high level flow diagrams that are used to explain various embodiments of the present invention.
Figure 2B:
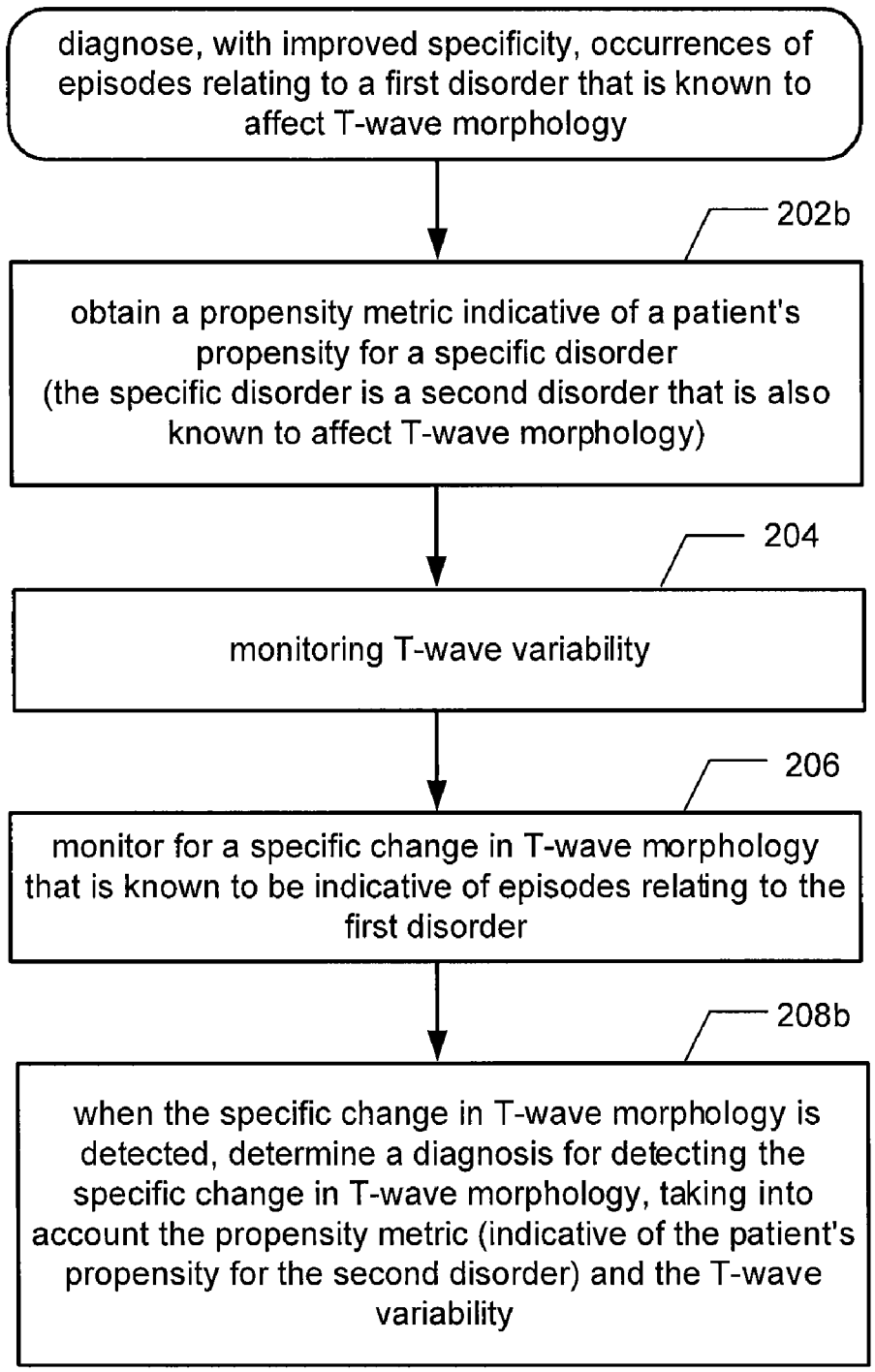

The high level flow diagrams of FIGS. 2A and 2B will now be used to summarize various embodiments of the present invention that relate to diagnosing, with improved specificity, occurrences of episodes relating to a "first disorder" that is known to affect T-wave morphology. Such a first disorder can be a primary disorder, or a comorbidity. Although not necessary, it will be assumed, for the discussion of the flow diagrams of FIGS. 2A and 2B, that patient has a propensity for the first disorder as well as a propensity for another (i.e., second) disorder. One of these disorders can be the primary disorder, and the other can be a comorbidity, or both the first and second disorders can be comorbidities.

Figure 2C:
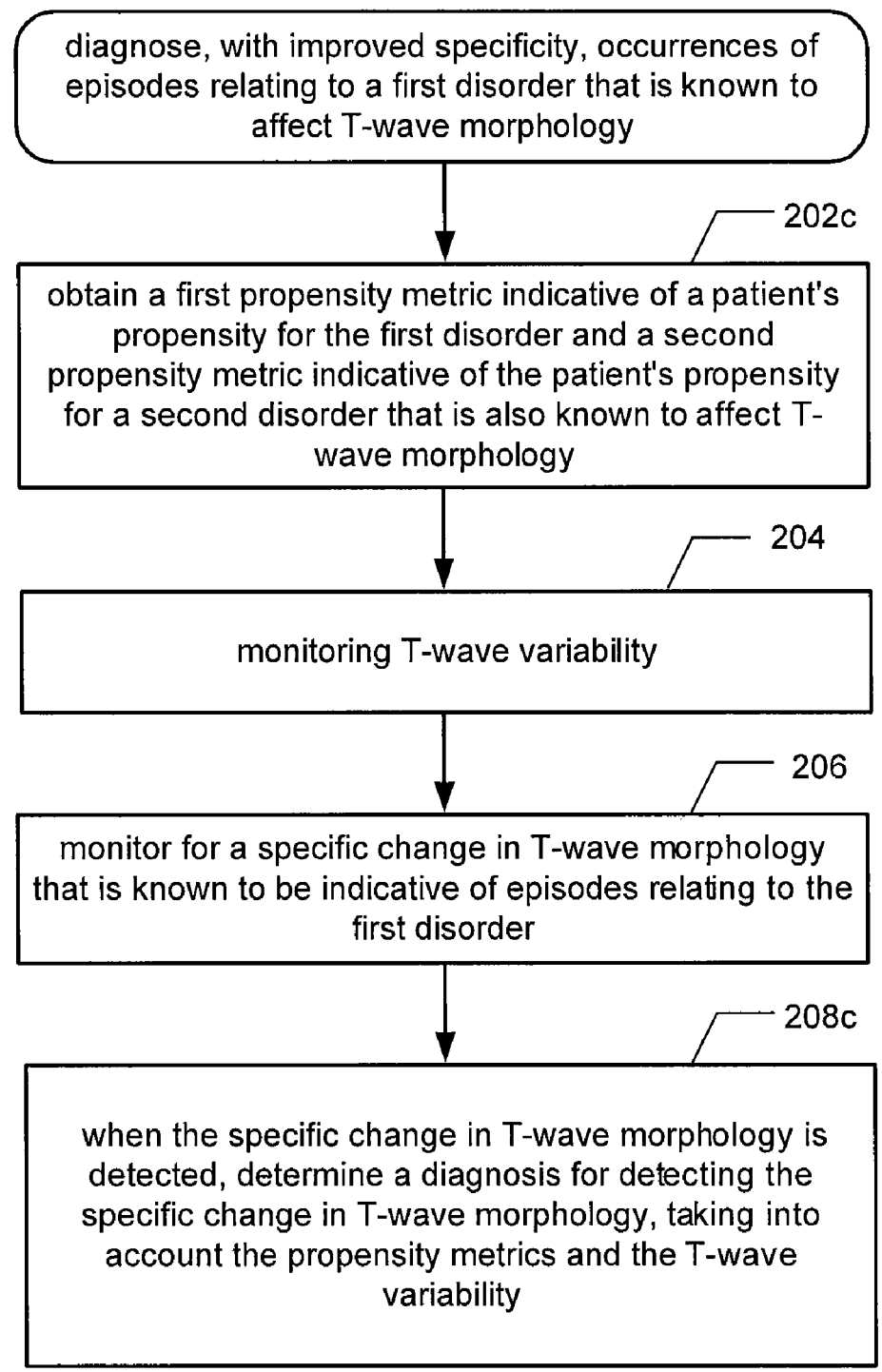

The flow diagrams of FIGS. 2A-2C provide an overview of the operation and novel features that can be implemented in various embodiments, e.g., of an implantable device and/or external device. In the flow diagrams, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the stimulation device. Those skilled in the art may readily write such a control program based on the flow diagram and other descriptions presented herein.

Where steps of the flow diagrams 2A-2C are the same, they are numbered the same. Where steps of these flow diagrams differ, the steps are labeled with either an "a", "b" or "c" following the base reference number.

Referring first to FIG. 2A, at step 202*a*, a propensity metric indicative of a patient's propensity for a specific disorder is obtained. The specific disorder can be the first disorder (for which there is an attempt to improve the specificity of diagnosing occurrences of episodes relating to the disorder). Alternatively, the specific disorder, for which a propensity metric is obtained, can be a second disorder that is also known to affect T-wave morphology, as indicated at step 202*b* in FIG. 2B.

For example, assume that there is a desire to improve the specificity of diagnosing occurrences of episodes relating to diabetes. Such episodes can be hyperglycemic episodes or hypoglycemic episodes, both of which can occur in diabetic patients. The propensity metric, obtained at step 202*a*, can be indicative of a patient's propensity for diabetes. Alternatively, the propensity metric, obtained at step 202*b*, can be indicative of the patient's propensity for another disorder, such as coronary artery disease, that is also known to affect T-wave morphology.

In certain embodiments the propensity metric can have one of four possible values, however use of more or less values is also within the scope of the present invention. The scale of the propensity metric can be selected as desired. For example, in one embodiment, the lowest propensity metric is 0 and the highest propensity metric is 1, i.e., the scale is 0-1. In another embodiment, the lowest propensity metric is 0 and the highest propensity metric is 3, i.e., the scale is 0-3. An example of a 0-3 scale is shown below in Table 1. Other scales are possible, and within the scope of the present invention.

TABLE 1

| Propensity Metric Value | Corresponding Condition |
| --- | --- |
| 0 | The patient has not been diagnosed with the disorder, and does not have a predisposition for developing the disorder later |
| 1 | The patient has not been diagnosed with the disorder, but the patient has a predisposition for developing the disorder later |
| 2 | The patient has not been diagnosed with the disorder, but the patient has a high risk of developing the disease later |
| 3 | The patient currently has been diagnosed with the disorder |

A physician can determine the propensity metric for a specific disorder, e.g., based on a patient's own history, the patient's family history, a questionnaire and/or tests performed on the patient. The propensity metric can be determined at the time of implant of an implantable cardiac device, and can be updated at follow-up visits.

Referring again to FIGS. 2A and 2B, as shown at step 204, a patient's T-wave variability is monitored. This can include determining a T-wave variability index (TVi), which can be determined on a continuous, periodic or aperiodic basis. The TVi, or more generally the T-wave variability, can be a measure of variability of one or more T-wave metric. Exemplary T-wave metrics, of which a variability can be calculated, include, but are not limited to: maximum amplitude of T-wave, minimum amplitude of T-wave, peak-to-peak amplitude of T-wave, location of maximum amplitude of T-wave, location of minimum amplitude of T-wave, area under T-wave, slope of T-wave, T-wave amplitude dispersion, T-wave centroid, QT interval, corrected QT interval, amplitude of ST segment, T-wave frequency content, and T-wave frequency spread. Another exemplary T-wave metric (whose variability can be determined and monitored) is QT max-QT end. There are various techniques that are known for identifying T-waves, thereby enabling measurement of the above mentioned T-wave metrics. Some exemplary techniques for detecting T-waves are disclosed in U.S. patent application Ser. No. 10/979,833, entitled "Systems and Methods for Automatically Setting Refractory and Blanking Periods," (Snell and Bharmi) filed Nov. 1, 2004, now abandoned, which is incorporated herein by reference. Some additional exemplary techniques for detecting T-waves are disclosed in U.S. Pat. No. 5,782,887 (van Krieken et al) and U.S. Pat. No. 6,836,682 (Van Dam), which are incorporated herein by reference. Use of alternative techniques for detecting T waves are also within the scope of the present invention.

For each of the above T-wave metrics, actual, absolute, normalized (e.g., to heart rate and/or R-wave amplitude), or otherwise adjusted values can be used. The monitored T-wave variability can be, e.g., a variability of any one of the above T-wave metrics, or a weighted average of the variability of multiple ones of the above T-wave metrics. In addition, or instead of using the above T-wave metrics, T-wave variability can be of isochoric points of the T-wave. T-wave variability may also be or include a measure of the variability of a magnitude of T-wave alternans. In other words, magnitudes of T-wave alternans can be a T-wave metric for which a measure of variability is determined.

T-wave variability can be determined by calculating a standard deviation, a pseudo random deviation, root mean-square differences, a range, a interquartile range, a mean difference, a median absolute deviation, an average absolute deviation, etc, of any of the above mentioned T-wave metrics, or combinations thereof, or other T-wave metrics. These are just a few examples, which are not meant to be limiting. Also, it is noted that most any known technique for determining heart rate variability (HRV), including but not limited to time domain, frequency domain, and non-linear techniques, can be used to determine T-wave variability by using measures of T-wave metrics in place of measures of RR intervals.

In specific embodiments, a T-wave variability can be determined at implant, or at some other time when the patient is known to not be experiencing any episodes of a disorder. This can be considered the patient's baseline T-wave variability.

When T-wave variability is monitored at step 204, this can include determining a value of T-wave variability, comparing the value of T-wave variability to one or more threshold, and/or comparing a difference between the value of T-wave variability and the baseline T-wave variability to a corresponding threshold. The baseline T-wave variability may also be updated from time to time, but preferably should be determined based on T-wave metrics obtained when the patient is not experiencing episodes of a disorder.

As mentioned to above, T-wave variability can be determined substantially continuous and/or periodically. For example, there can be a running value of T-wave variability. Additionally, or alternatively, T-wave variability can be determined every 5 minutes, hourly, daily, weekly and/or monthly, etc. T-wave variability can be determined for a single window of time (e.g., 5 minute window or hour window, etc), or for multiple windows of time (e.g., 5 minute and 1 hour windows, etc).

Through experimentation, a specific disorder's affect on T-wave variability can be determined. For example, the inventors have determined that a baseline T-wave variability for diabetics is higher than normal, and that QT-interval increases further during episodes of hypoglycemia. For other disorders, it may be determined that T-wave variability does not increase, or at least not significantly, during episodes of the disorder. It may even be determined that T-wave variability stays the same or decreases during episodes of a certain disorder. From this, it can be appreciated that by monitoring T-wave variability, the specificity of a diagnosis can be improved, if T-wave variability is taken into account when determining the diagnosis.

Still referring to FIGS. 2A and 2B, at step 206, monitoring for a specific change in T-wave morphology is performed, where the specific change in T-wave morphology is known to be indicative of episodes relating to the first disorder. For example, it is known that QT interval prolongation is indicative of hypoglycemic episodes, and that an increase in corrected QT interval dispersion is indicative of hyperglycemic episodes. Thus, at step 206, if the patient has diabetes (i.e., assume the first disorder referred to in FIGS. 2A-2C is diabetes), then an elongation of the QT interval and/or an increase in correct QT interval dispersion can be monitored for at step 206. Additional examples are discussed below.

As specified at steps 208a and 208b, when the specific change in T-wave morphology is detected (e.g., ST segment depression), a diagnosis for detecting the specific change in T-wave morphology is determined, taking into account the propensity metric and the T-wave variability. Steps 208a and 208b differ in that in step 208a, the propensity metric relates to the first disorder, and in step 208b the propensity metric relates to the second disorder that is also known to affect T-wave morphology. The differences between these will be explained by way of a few examples.

For example, assume that a patient is likely to develop a kidney disfunction disorder, and that the desire is to detect hypokelemic episodes with increased specificity. It is known that during a hypokelemic episode a patient typically exhibits ST segment depression. Note that it is also known that during an episode of angina, which occur in patients having coronary artery disease, a patient also typically exhibits ST segment depression. In one embodiment, the propensity metric obtained at step 202a can be indicative of the patient's propensity for kidney disfunction. Where that is the case, if ST segment depression is detected, then at step 208a, the patient's propensity for kidney disfunction, and the monitored T-wave variability, are taken into account when determining the diagnosis for the detected ST segment depression. Also, assume that it has been determined how hypokelemic episodes affect T-wave variability (e.g., hypokelemic episodes increase T-wave variability). If the patient has a high propensity for kidney disfunction, the patient's T-wave variability is high (or relatively high compared to the baseline), then a diagnosis that the patient experienced a hypokalemic episode can be made with high confidence.

In another example, assume again that a patient is likely to develop a kidney disfunction disorder, and that the desire is to detect hypokalemic episodes with increased specificity. Again, assume that it has been determined how hypokelemic episodes affect T-wave variability (e.g., assume hypokelemic episodes increase T-wave variability). However, here assume that the propensity metric obtained at step 202b is indicative of the patient's propensity for coronary artery disease, which as mentioned above, reveals itself as episodes of angina. As also mentioned above, episodes of angina typically cause ST segment depression. If the patient has a high propensity for coronary artery disease, and the T-wave variability is high (or relatively high compared to the baseline), then at step 208b a diagnosis that the patient experienced a hypokalemic episode (when ST segment depression is detected) may be made with low confidence, since there is a fairly good likelihood that an episode of angina may have caused the ST segment depression. However, if the patient has no propensity, or a very low propensity for angina, then at step 208b a diagnosis that the patient experienced a hypokalemic episode (when ST segment depression is detected) can be made with high confidence, since it is unlikely that it was an episode of angina that caused the ST segment depression. In this last example, if the patient's T-wave variability were relatively low (or more generally, the T-wave variability is not what is expected for an episode of a hypokalemic episode), then the confidence level of the diagnosis can be affected.

It also possible to obtain multiple propensity metrics, and that the multiple propensity metrics can be taken into account, along with T-wave variability, when producing a diagnosis for detecting a specific change in T-wave morphology. Continuing with the above example, if the patient has a high propensity for kidney disfunction, and a low propensity for coronary artery disease, then a detection of ST segment depression and high T-wave variability can be diagnosed as a hypokalemic episode with high confidence. However, if the patient has a medium propensity for kidney disfunction, and a medium propensity for coronary artery disease, then a detected ST segment depression can be diagnosed as a hypokalemic episode with medium confidence. A summary of such embodiments is provided in FIG.

An exemplary algorithm for determining a diagnosis is:

$$\text{diagnosis score for disorder}_n = (\text{propensity} * \text{weight1}) + (TVi * \text{weight2}) + (\text{presence of expected change in T-wave morphology} * \text{weight3}).$$

There can be a similar algorithm for each disorder that is being monitored for. The "diagnosis score" can be compared to one or more threshold, to determine whether a specific diagnosis should be made, and/or to determine a confidence level of a diagnosis. Multiple propensities, each having a different weight, can be used in such an algorithm. Where the presence of something (e.g., a certain T-wave morphology, or a high TVi) makes a diagnosis less likely, negative weighting factors can be used. The above algorithm is just one example of an algorithm that can be used at steps 208a, 208b and 208c. One of ordinary skill in the art reading this disclosure will understand that numerous alternative algorithms can be used that take into account one or more propensity metric and T-wave variability, when producing a diagnosis. Use of such alternative algorithms is within the scope of the present invention.

As mentioned above, embodiments of the present invention can be used to diagnose, with improved specificity, occurrences of episodes relating to disorders that are known to affect T-wave morphology. Exemplary disorders include, but are not limited to, diabetes, myocardial ischemia, kidney disfunction, coronary artery disease, diastolic heart failure, systolic heart failure, myocardial inhomgeneity and various electrolytic imbalances. Exemplary details of how embodiments of the present invention can be used to detect hypokalemic episodes, in patients that have or are likely to develop a kidney dysfunction disorder, were provided above. Additional details of how the present invention can be used to diagnose occurrences of episodes of some of the other exemplary disorders are provided below, again with reference to FIGS. 2A-2C.

Where a patient has diabetes, or may develop diabetes, embodiments of the present invention can be used to diagnose, with improved specificity, hypoglycemic episodes. Referring to FIG. 2A, the propensity metric obtained at step 202a can be indicative of the patient's propensity for diabetes. Alternatively (as indicated at step 202b in FIG. 2B), or additionally (as indicated at step 202c in FIG. 2C), an obtained propensity metric can be indicative of the patient's propensity for a second disorder that is also known to affect T-wave morphology. It is known that during hypoglycemic episodes, a patient typically experiences QT interval prolongation. Also, assume that it has been determined that hypoglycemic episodes increase T-wave variability. Accordingly, at step 206 (in FIGS. 2A-2C), the specific change in T-wave morphology that is monitored for can be QT interval prolongation. At step 208a (in FIG. 2A), when a prolongation of the QT interval (e.g., beyond a threshold) is detected, a diagnosis for detecting QT interval prolongation can be made, taking into account the patient's propensity for diabetes and the correspond T-wave variability (determined at step 206). Alternatively, at step 208b (in FIG. 2B), when QT interval prolongation is detected, a diagnosis for such a detection can be made, taking into account the patient's propensity for another disorder (besides diabetes) and the correspond T-wave variability (determined at step 206). In still another embodiment, at step 208c (in FIG. 2C), when QT interval prolongation is detected, a diagnosis for detecting QT interval prolongation can be made, taking into account the patient's propensity for diabetes and the patient's propensity for another disorder (besides diabetes), and the correspond T-wave variability.

When the patient has diabetes, or may develop diabetes, embodiments of the present invention can also be used to diagnose, with improved specificity, hyperglycemic episodes, which are known to typically cause an increase in corrected QT (QTc) interval dispersion. Accordingly, at step 206 (in FIGS. 2A-2C), the specific change in T-wave morphology that is monitored for can be an increase in QTc interval dispersion. Also, assume that it has been determined that hyperglycemic episodes increase T-wave variability. At step 208a (in FIG. 2A), when an increase in QTc interval dispersion (e.g., beyond a threshold) is detected, a diagnosis for detecting the increase in QTc interval dispersion can be made, taking into account the patient's propensity for diabetes and the correspond T-wave variability (determined at step 206). Alternatively, at step 208b (in FIG. 2B), the diagnosis for such a detection can be made, taking into account the patient's propensity for another disorder (besides diabetes) and the correspond T-wave variability (determined at step 206). In still another embodiment, at step 208c (in FIG. 2C), when the increase in QTc interval dispersion is detected, a diagnosis can be made, taking into account the patient's propensity for diabetes and the patient's propensity for another disorder (besides diabetes), and the correspond T-wave variability.

Where a patient has or may develop myocardial ischemia, embodiments of the present invention can be used to diagnose, with improved specificity, ischemic episodes. Referring to FIG. 2A, the propensity metric obtained at step 202a can be indicative of the patient's propensity for myocardial ischemia. Alternatively (as indicated at step 202b in FIG. 2B), or additionally (as indicated at step 202c in FIG. 2C), an obtained propensity metric can be indicative of the patient's propensity for a second disorder that is also known to affect T-wave morphology. It is known that during ischemic episodes, a patient typically experiences ST segment deviation. Accordingly, at step 206 (in FIGS. 2A-2C), the specific change in T-wave morphology that is monitored for can be ST segment deviation. Also, assume that it has been determined how hypoglycemic episodes affect T-wave variability. At step 208a (in FIG. 2A), when a deviation of the ST interval (e.g., beyond a threshold) is detected, a diagnosis for detecting ST segment deviation can be made, taking into account the patient's propensity for myocardial ischemia and the correspond T-wave variability (determined at step 206). Alternatively, at step 208b (in FIG. 2B), when ST segment deviation is detected, a diagnosis for such a detection can be made, taking into account the patient's propensity for another disorder (besides myocardial ischemia) and the correspond T-wave variability (determined at step 206). In still another embodiment, at step 208c (in FIG. 2C), when ST segment deviation is detected, a diagnosis for such a detection can be made, taking into account the patient's propensity for myocardial ischemia and the patient's propensity for another disorder (besides myocardial ischemia), and the correspond T-wave variability.

Provided above was a discussion of how to increase the specificity of diagnosing episodes of hypokalemic episodes for patient's that have or are likely to develop a kidney dysfunction disorder. Such patient's may also experience hyperkalemic episodes, which are known to typically cause ST segment elevation. Accordingly, embodiments of the present invention can be used to diagnose, with improved specificity, hyperkalemic episodes. Referring to FIG. 2A, the propensity metric obtained at step 202a can be indicative of the patient's propensity for kidney dysfunction. Alternatively (as indicated at step 202b in FIG. 2B), or additionally (as indicated at step 202c in FIG. 2C), an obtained propensity metric can be indicative of the patient's propensity for a second disorder that is also known to affect T-wave morphology. As mentioned above, it is known that during hyperkalemic episodes, a patient typically experiences ST segment elevation. Accordingly, at step 206 (in FIGS. 2A-2C), the specific change in T-wave morphology that is monitored for can be ST segment elevation. Also, assume that it has been determined how hyperkalemic episodes affect T-wave variability. At step 208a (in FIG. 2A), when an elevation of the ST interval (e.g., beyond a threshold) is detected, a diagnosis for detecting ST segment elevation can be made, taking into account the patient's propensity for kidney dysfunction and the corresponding T-wave variability (determined at step 206). Alternatively, at step 208b (in FIG. 2B), when ST segment elevation is detected, a diagnosis for such a detection can be made, taking into account the patient's propensity for another disorder (besides kidney dysfunction) and the corresponding T-wave variability (determined at step 206). In still another embodiment, at step 208c (in FIG. 2C), when ST segment elevation is detected, a diagnosis for such a detection can be made, taking into account the patient's propensity for kidney dysfunction and the patient's propensity for another disorder (besides kidney dysfunction), and the correspond T-wave variability.

Where a patient has or may develop coronary artery disease, embodiments of the present invention can be used to diagnose, with improved specificity, episodes of angina. Referring to FIG. 2A, the propensity metric obtained at step 202a can be indicative of the patient's propensity for coronary artery disease. Alternatively (as indicated at step 202b in FIG. 2B), or additionally (as indicated at step 202c in FIG. 2C), an obtained propensity metric can be indicative of the patient's propensity for a second disorder that is also known to affect T-wave morphology. It is known that during episodes of angina, a patient typically experiences ST segment depression. Accordingly, at step 206 (in FIGS. 2A-2C), the specific change in T-wave morphology that is monitored for can be ST segment depression. Also, assume that it has been determined how episodes of angina affect T-wave variability. At step 208a (in FIG. 2A), when a depression of the ST segment (e.g., beyond a threshold) is detected, a diagnosis for detecting ST segment depression can be made, taking into account the patient's propensity for coronary artery disease and the corresponding T-wave variability (determined at step 206). Alternatively, at step 208b (in FIG. 2B), when ST segment depression is detected, a diagnosis for such a detection can be made, taking into account the patient's propensity for another disorder (besides coronary artery disease) and the corresponding T-wave variability (determined at step 206). In still another embodiment, at step 208c (in FIG. 2C), when ST segment depression is detected, a diagnosis for detecting ST segment depression can be made, taking into account the patient's propensity for coronary artery disease and the patient's propensity for another disorder (besides coronary artery disease), and the corresponding T-wave variability.

Based on the above discussion, one of ordinary skill in the art will appreciate how embodiments of the present invention can be used to increase the specificity of diagnosing episodes of disorders, other than those discussed in detail above. For example, embodiments of the present invention can also be used to diagnose episodes of diastolic heart failure, systolic heart failure, myocardial inhomogeneity, and various electrolytic imbalances, with increased specificity. Also, in the above discussion, exemplary indicators of each disorder were discussed (e.g., ST segment depression is indicative of episodes of angina). However, monitoring for other indicators and/or additional indicators, other than those mentioned above, are also within the scope of the present invention.

Embodiments of the present invention can be used to monitor for a plurality of different specific changes in T-wave morphology at the same time, where each monitored for change in T-wave morphology is know to be indicative an episode relating to a disorder (e.g., a first change may correspond to an episode of a first disorder, a second change may correspond to an episode of a second disorder, etc.). In other words, multiple instances of embodiments of the present invention can occur in parallel. Then, whenever a change in T-wave morphology is detected, a diagnosis can be made for the detection, taking into account one or more propensity metric and the patient's T-wave variability.

More generally, embodiments of the present invention described above can be used to produce a diagnosis, taking into account T-wave morphology, T-wave variability and one or more propensity metric. Such embodiments should provide for improved specificity of a diagnosis.

When an episodes of a disorder is detected, information about the episode, including but not limited to the time of the episode, the length of the episode, information about the detected change in T-wave morphology, T-wave variability (e.g., TVi) and the like, can be stored for later retrieval and/or analysis, e.g., by a physician. Additionally, depending on what episode is detected, an alarm and/or therapy can be triggered. The above described embodiments of the present invention do not relate to the specific alarms and/or therapy that are triggered. Rather, the above described embodiments of the present invention relate to increasing the specificity of diagnosing the occurrences of such episodes, e.g., so that more specific and appropriate therapy can be delivered.

Figure 3:
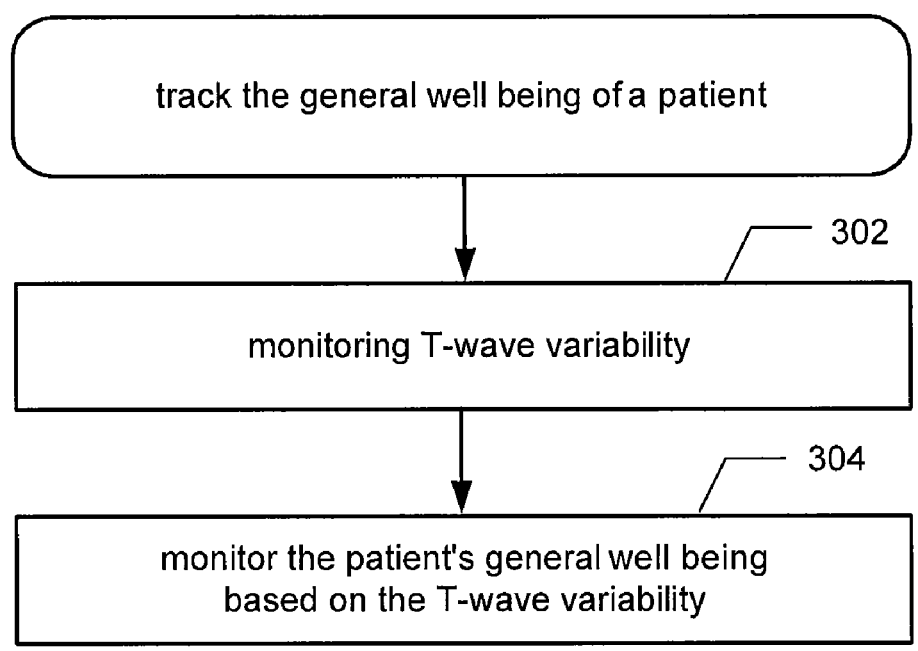
FIG. 3 is a high level flow diagram is used to explain how measures of T-wave variability can be used to monitor a patient's general well being, in accordance with an embodiment of the present invention.

As described with reference to the high level flow diagram of FIG. 3, a metric of T-wave variability (e.g., TVi) can also be used to track the general well being of the patient. This can include monitoring T-wave variability at step 302, which can include monitoring the time course of its change away and back to baseline. Then, based on the T-wave variability, the general well being of the patient can be monitored, as indicated at step 304. Information about T-wave variability can thus be saved and trended. It is expected a patient's T-wave variability will decrease, if a patient's general well being improves, and vice versa. Accordingly, an increase in TVi can be interpreted as being indicative of a worsening of a patient's general well being, and a decrease in TVi can be interpreted as being indicative of improvement of a patient's general well being.

Figure 4:
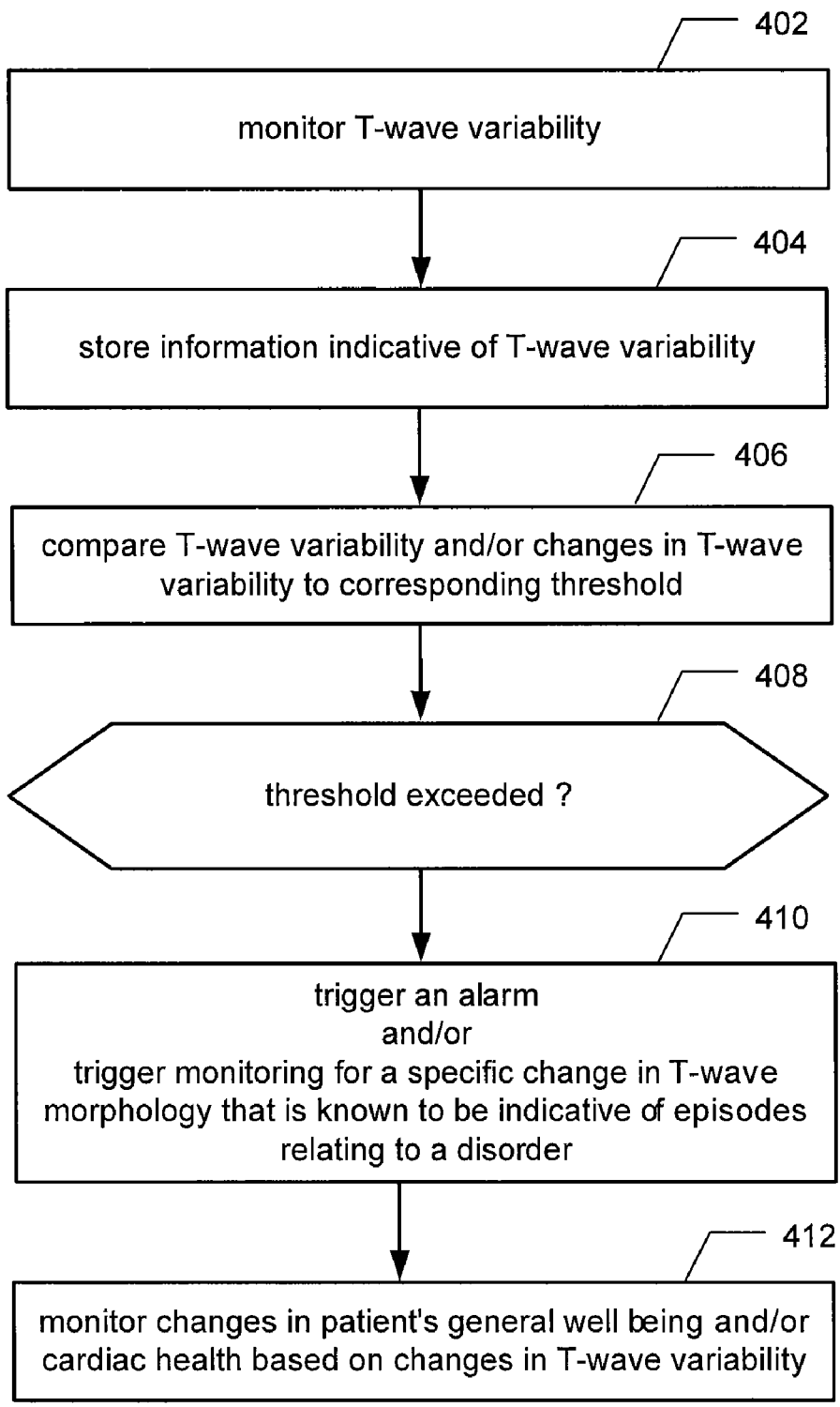
FIG. 4 is a high level flow diagram that is used to explain how measures of T-wave variability can be used to trigger the monitoring of a disorder, to monitor a patient's cardiac health and/or to monitor a patient's general well being, in accordance with embodiments of the present invention.

In certain embodiments, measures of T-wave variability can be used as a trigger to monitor for episodes relating to a disorder that is known to affect T-wave morphology. In other words, when T-wave variability exceeds a specified threshold, this can trigger attempting to determine the cause of the increase in T-wave variability. This can also trigger an alarm. More specifically, referring to FIG. 4, measures of T-wave variability can be used to trigger an alarm and/or the monitoring for a specific change in T-wave morphology that is known to be indicative of episodes relating to a disorder, as indicated at steps 406-410 of FIG. 4. More generally, when T-wave variability, or a change therein, exceeds a corresponding threshold, a diagnosis can be produced. For example, as was described above, the diagnosis can be produced taking into account T-wave morphology, T-wave variability and propensity metrics. Additionally, information that is indicative of the T-wave variability can be stored, as indicated at step 404, and changes in the T-wave variability over time can be monitored based on the stored information, as indicated at steps 412. Also, at step 412, a patient's cardiac health and/or general well being can be monitored based on the changes in T-wave variability. This can include interpreting increases in T-wave variability as being indicative of a worsening of a patient's cardiac health (and/or general well being), and interpreting decreases in T-wave variability as being indicative of an improvement of the patient's cardiac health (and/or general well being).

Exemplary Implantable System

Figure 5:
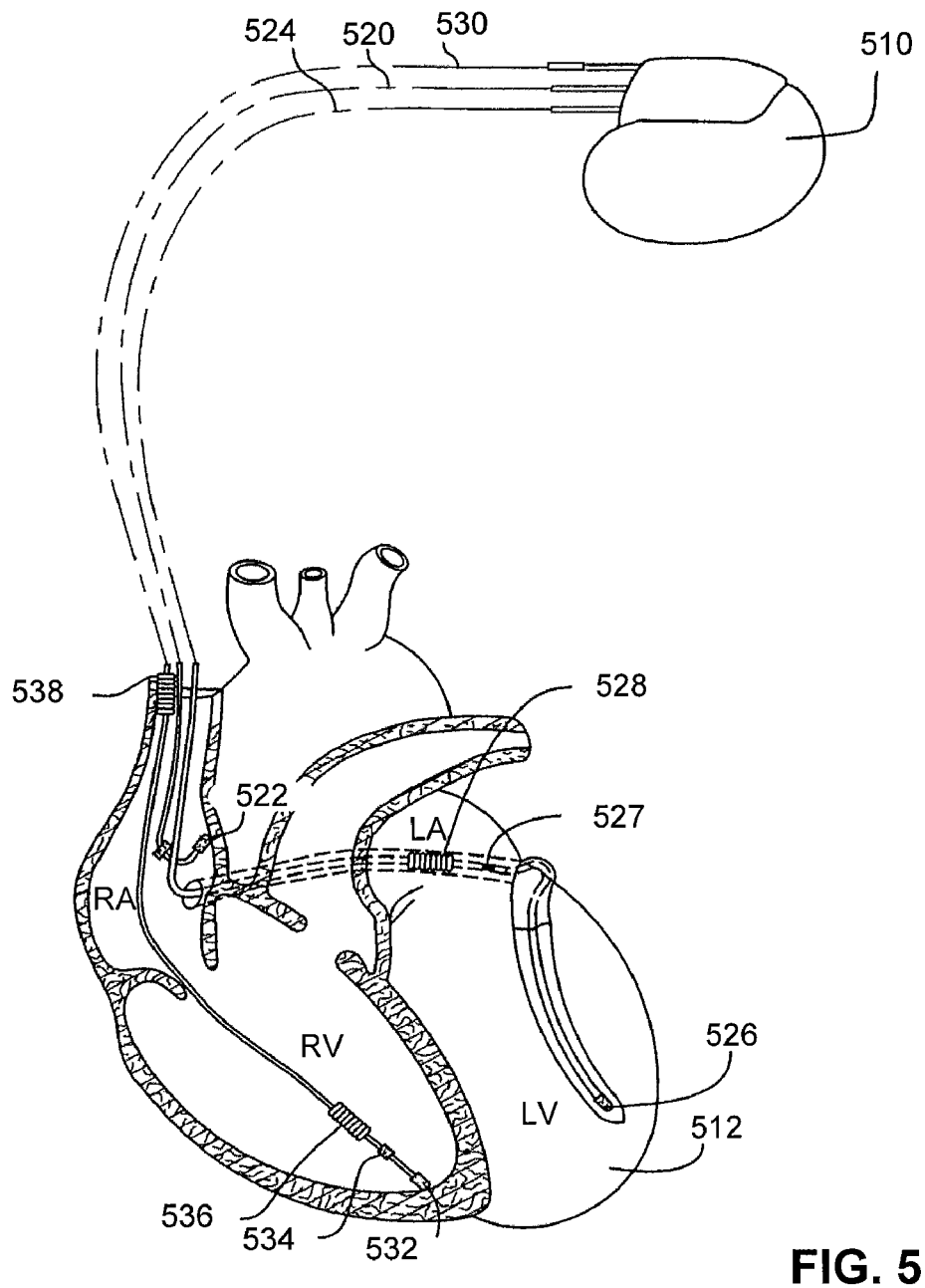
FIG. 5 is a simplified, partly cutaway view illustrating an exemplary implantable stimulation device that can be used to implement embodiments of the present invention, where the device is in electrical communication with at least three leads implanted into a patient's heart for delivering multi-chamber stimulation and shock therapy.
Figure 6:
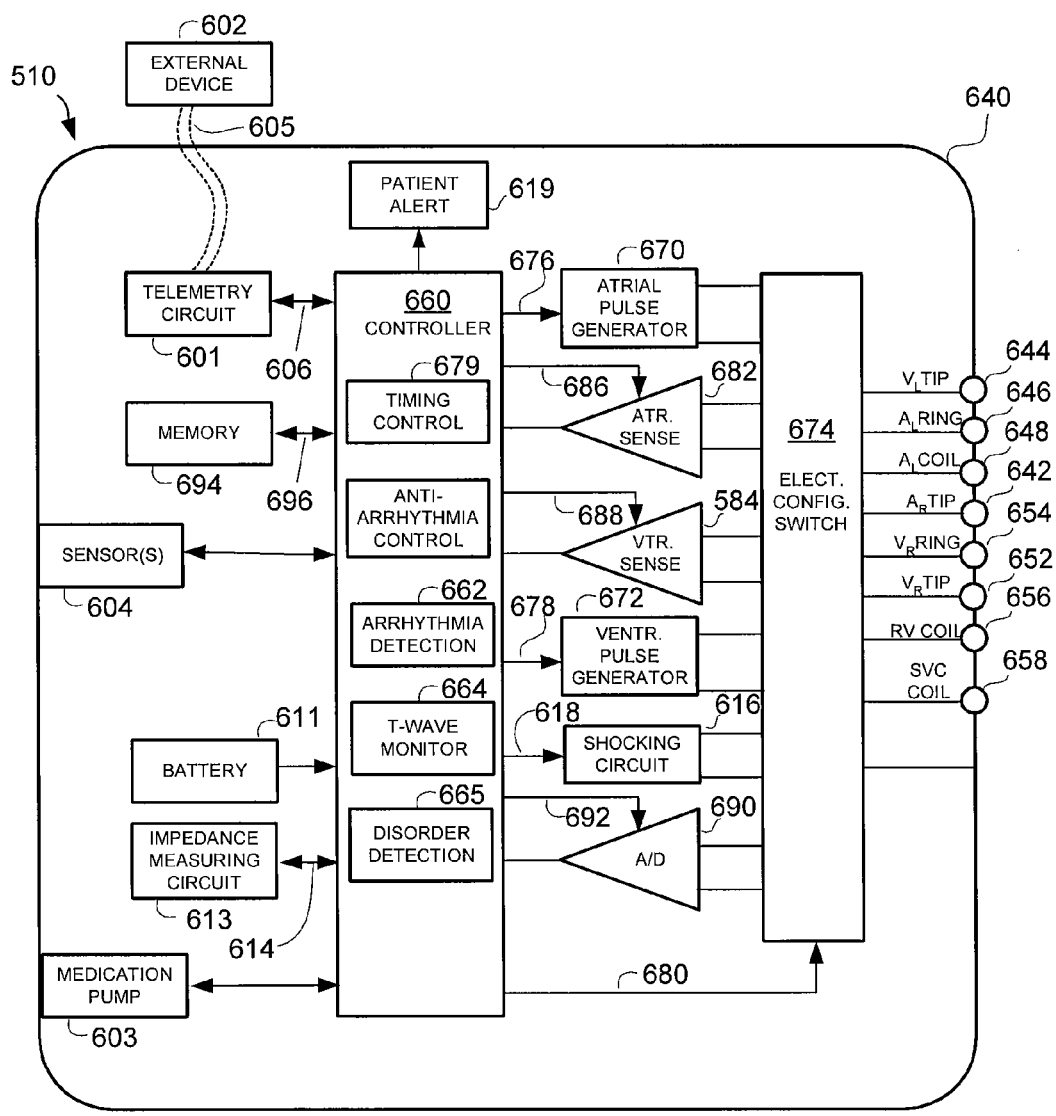
FIG. 6 is a functional block diagram of the multi-chamber implantable stimulation device of FIG. 5, illustrating the basic elements that provide pacing stimulation, cardioversion, and defibrillation in four chambers of the heart.

FIGS. 5 and 6 will now be used to describe an exemplary implantable system that can be used to implement the embodiments of the present invention which were described above. Referring to FIG. 5, the implantable system is shown as including an implantable stimulation device 510, which can be a pacing device and/or an implantable cardioverter defibrillator. The device 510 is shown as being in electrical communication with a patient's heart 512 by way of three leads, 520, 524 and 530, which can be suitable for delivering multi-chamber stimulation and shock therapy.

Still referring to FIG. 5, to sense atrial cardiac signals and to provide right atrial chamber stimulation therapy, the device 510 is coupled to an implantable right atrial lead 520 having at least an atrial tip electrode 522, which typically is implanted in the patient's right atrial appendage. To sense left atrial and ventricular cardiac signals and to provide left-chamber pacing therapy, the device 510 is coupled to a "coronary sinus" lead 524 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 328.

The device 510 is also shown in electrical communication with the patient's heart 512 by way of an implantable right ventricular lead 530 having, in this embodiment, a right ventricular tip electrode 532, a right ventricular ring electrode 534, a right ventricular (RV) coil electrode 336, and an SVC coil electrode 538. Typically, the right ventricular lead 530 is transvenously inserted into the heart 512 so as to place the right ventricular tip electrode 532 in the right ventricular apex so that the RV coil electrode 536 will be positioned in the right ventricle and the SVC coil electrode 338 will be positioned in the superior vena cava. Accordingly, the right ventricular lead 530 is capable of receiving cardiac signals and delivering stimulation in the form of pacing and shock therapy to the right ventricle.

FIG. 6 will now be used to provides some exemplary details of the components of the implantable devices 510. Referring now to FIG. 6, each of the above implantable devices 510, and alternative versions thereof, can include a microcontroller 660. As is well known in the art, the microcontroller 660 typically includes a microprocessor, or equivalent control circuitry, and can further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design of the microcontroller 660 are not critical to the present invention. Rather, any suitable microcontroller 660 can be used to carry out the functions described herein. The use of microprocessor-based control circuits for performing timing and data analysis functions are well known in the art. In specific embodiments of the present invention, the microcontroller 660 performs some or all of the steps associated monitoring T-wave variability, and with diagnosing, with improved specificity, occurrences of episodes relating to disorders that are known to affect T-wave morphology. Additionally, the microcontroller can be used to monitor changes in the cardiac health of a patient based changes in T-wave variability.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 510 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 640, shown schematically in FIG. 6, is often referred to as the "can", "case" or "case electrode" and may be programmably selected to act as the return electrode for all "unipolar" modes. The housing 640 may further be used as a return electrode alone or in combination with one or more of the coil electrodes, 128, 136 and 138, for shocking purposes. The housing 640 can further include a connector (not shown) having a plurality of terminals, 642, 644, 646, 648, 652, 654, 656, and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 522.

To achieve left atrial and ventricular sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 526, the left atrial tip electrode 527, and the left atrial coil electrode 528, respectively.

To support right ventricle sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 532, right ventricular ring electrode 534, the RV coil electrode 536, and the SVC coil electrode 538, respectively.

An atrial pulse generator 670 and a ventricular pulse generator 672 generate pacing stimulation pulses for delivery by the right atrial lead 520, the right ventricular lead 530, and/or the coronary sinus lead 524 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators, or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry 679 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, etc.) by selectively closing the appropriate combination of switches (not shown) as is known in the art.

Atrial sensing circuits 682 and ventricular sensing circuits 684 may also be selectively coupled to the right atrial lead 520, coronary sinus lead 524, and the right ventricular lead 530, through the switch 674 for detecting the presence of cardiac activity in each of the four chambers of the heart.

Accordingly, the atrial (ATR. SENSE) and ventricular (VTR. SENSE) sensing circuits, 682 and 684, may include dedicated sense amplifiers, multiplexed amplifiers, or shared amplifiers. The switch 674 determines the "sensing polarity" of the cardiac signal by selectively closing the appropriate switches, as is also known in the art. In this way, the clinician may program the sensing polarity independent of the stimulation polarity.

Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables the device 510 to deal effectively with the difficult problem of sensing the low amplitude signal characteristics of atrial or ventricular fibrillation. Such sensing circuits, 682 and 684, can be used to determine cardiac performance values used in the present invention. Alternatively, an automatic sensitivity control circuit may be used to effectively deal with signals of varying amplitude.

The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity, in the appropriate chambers of the heart. The sensing circuits, 682 and 684, in turn, receive control signals over signal lines, 686 and 688, from the microcontroller 660 for purposes of measuring cardiac performance at appropriate times, and for controlling the gain, threshold, polarization charge removal circuitry (not shown), and timing of any blocking circuitry (not shown) coupled to the inputs of the sensing circuits, 682 and 686.

One or more sensor 604 that measures a physiologic property can be located within the housing 640 of the implantable device 510, or connected to the housing 640.

For arrhythmia detection, the device 510 includes an arrhythmia detector 662 that utilizes the atrial and ventricular sensing circuits, 682 and 684, to sense cardiac signals to determine whether a rhythm is physiologic or pathologic. The timing intervals between sensed events (e.g., P-waves, R-waves, and depolarization signals associated with fibrillation) can be classified by the microcontroller 660 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 662 can be implemented within the microcontroller 660, as shown in FIG. 6. Thus, this detector 662 can be implemented by software, firmware, or combinations thereof. It is also possible that all, or portions, of the arrhythmia detector 662 can be implemented using hardware. Further, it is also possible that all, or portions, of the ischemia detector 662 can be implemented separate from the microcontroller 660.

In accordance with embodiments of the present invention, the implantable device 510 includes T-wave monitor 664, which can monitor variability in one or more T-wave metric. Exemplary T-wave metrics, of which a variability can be calculated, include, but are not limited to: maximum amplitude of T-wave, minimum amplitude of T-wave, peak-to-peak amplitude of T-wave, location of maximum amplitude of T-wave, location of minimum amplitude of T-wave, area under T-wave, slope of T-wave, T-wave amplitude dispersion, T-wave centroid, QT interval, corrected QT interval, amplitude of ST segment, T-wave frequency content, T-wave frequency spread, and QT max-QT end. The monitor 664 can also monitor for specific changes in T-wave morphology that are known to be indicative of specific disorders, many of which were discussed above. The monitor 664 can be implemented within the microcontroller 660, as shown in FIG. 6, and can the be implemented by software, firmware, or combinations thereof. It is also possible that all, or portions, of the monitor 664 to be implemented using hardware. Further, it is also possible that all, or portions, of the monitor 664 to be implemented separate from the microcontroller 660.

The implantable device can also include a disorder detector 665, which can diagnose the detection of a specific change in T-wave morphology, with improved specificity, by taking into account T-wave variability and one or more propensity metric, as was described in great detail above. The detector 665 can be implemented within the microcontroller 660, as shown in FIG. 6, and can the be implemented by software, firmware, or combinations thereof. It is also possible that all, or portions, of the detector 665 to be implemented using hardware. Further, it is also possible that all, or portions, of the detector 665 to be implemented separate from the microcontroller 660.

The implantable device can also include a medication pump 603, which can deliver medication to a patient when episodes of specific disorder(s) are detected. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 6, cardiac signals are also applied to the inputs of an analog-to-digital (A/D) data acquisition system 690. The data acquisition system 690 is configured to acquire IEGM and/or ECG signals, convert the raw analog data into a digital signal, and store the digital signals for later processing and/or telemetric transmission to an external device 602. The data acquisition system 690 can be coupled to the right atrial lead 320, the coronary sinus lead 524, and the right ventricular lead 530 through the switch 674 to sample cardiac signals across any pair of desired electrodes.

The data acquisition system 690 can be coupled to the microcontroller 660, or other detection circuitry, for detecting an evoked response from the heart 412 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 660 detects a depolarization signal during a window following a stimulation pulse, the presence of which indicates that capture has occurred. The microcontroller 660 enables capture detection by triggering the ventricular pulse generator 672 to generate a stimulation pulse, starting a capture detection window using the timing control circuitry 679 within the microcontroller 660, and enabling the data acquisition system 690 via control signal 692 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 660 is further coupled to the memory 694 by a suitable data/address bus 696, wherein the programmable operating parameters used by the microcontroller 660 are stored and modified, as required, in order to customize the operation of the implantable device 510 to suit the needs of a particular patient. The memory 694 can also be used to store information about T-wave variability, and information about diagnosed episodes relating to disorders. The memory 694 can also store information related to the patient's cardiac health and/or general well being, as determined in accordance with embodiments of the present invention. Additionally, the memory 694 can be used to store propensity metrics, discussed above, which are indicative of a patient's propensity for specific disorders.

A telemetry circuit 601 can be used to wirelessly transmit such data to an external device 602, such as a programmer, monitor, transtelephonic transceiver, or a diagnostic system analyzer. The telemetry circuit can send data indicative of T-wave variability, diagnosed episodes relating to disorders, as determined in accordance with embodiments of the present invention, to the external device 602. Alternatively, the telemetry circuit 601 can transmit data indicative measures of T-wave morphology, and the external device 602 can determine the T-wave variability, changes in the same, and detect specific changes in T-waves that are known to be indicative of episodes relating to specific disorders. Accordingly, it can be the external device 602 that diagnoses, with improved specificity, occurrences of episodes relating to disorders that are known to affect T-wave morphology. The external device 602 can also monitor changes in a patient's general well being, based on changes in the patient's T-wave variability.

The operating parameters of the implantable device 510 may be non-invasively programmed into the memory 694 through the telemetry circuit 601 in telemetric communication with an external device 602. The telemetry circuit 601 can be activated by the microcontroller 660 by a control signal 606. The telemetry circuit 601 advantageously allows intracardiac electrograms and status information relating to the operation of the device 510 (as contained in the microcontroller 660 or memory 694) to be sent to the external device 602 through an established communication link 605.

For examples of telemetry devices, see U.S. Pat. No. 4,809, 697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 510 additionally includes a battery 611 which provides operating power to all of the circuits shown in FIG. 6. If the implantable device 510 also employs shocking therapy, the battery 611 should be capable of operating at low current drains for long periods of time, and then be capable of providing high-current pulses (for capacitor charging) when the patient requires a shock pulse. The battery 611 should also have a predictable discharge characteristic so that elective replacement time can be detected.

The implantable device 510 can also include a magnet detection circuitry (not shown), coupled to the microcontroller 660. It is the purpose of the magnet detection circuitry to detect when a magnet is placed over the implantable device 510, which magnet may be used by a clinician to perform various test functions of the implantable device 510 and/or to signal the microcontroller 660 that the external programmer 602 is in place to receive or transmit data to the microcontroller 660 through the telemetry circuits 601.

As further shown in FIG. 6, the device 510 is also shown as having an impedance measuring circuit 613 which is enabled by the microcontroller 660 via a control signal 614. The known uses for an impedance measuring circuit 613 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 613 is advantageously coupled to the switch 674 so that any desired electrode may be used. The impedance measuring circuit 613 is not critical to the present invention and is shown only for completeness.

In the case where the implantable device 510 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 660 further controls a shocking circuit 616 by way of a control signal 618. The shocking circuit 616 generates shocking pulses of low (up to 0.5 Joules), moderate (0.5-10 Joules), or high energy (11 to 40 Joules), as controlled by the microcontroller 660. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 640 may act as an active electrode in combination with the RV electrode 336, or as part of a split electrical vector using the SVC coil electrode 338 or the left atrial coil electrode 328 (i.e., using the RV electrode as a common electrode).

The above described implantable device 510 was described as an exemplary pacing device. One or ordinary skill in the art would understand that embodiments of the present invention can be used with alternative types of implantable devices. Accordingly, embodiments of the present invention should not be limited to use only with the above described device. For example, the implantable device 510 can be a simple monitoring device that does not provide any type of cardiac stimulation.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2A-2C, 3 and 4. Further, it is possible to change the order of some of the steps, without substantially changing the overall events and results. For another example, it is possible to change the boundaries of some of the blocks shown in FIG. 6.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A method for diagnosing, with improved specificity, occurrences of episodes relating to a first disorder that is known to affect T-wave morphology, the method comprising:
   (a) obtaining a propensity metric indicative of a patient's propensity for a specific disorder, where the specific disorder is either the first disorder or a second disorder that is also known to affect T-wave morphology;
   (b) monitoring T-wave variability;
   (c) monitoring for a specific change in T-wave morphology that is known to be indicative of episodes relating to the first disorder; and
   (d) when the specific change in T-wave morphology is detected, using a microprocessor to determine a diagnosis for detecting the specific change in T-wave morphology, taking into account the propensity metric and the T-wave variability.

2. The method of claim 1, wherein the determining the diagnosis at step (d) includes determining a level of confidence corresponding to the diagnosis.

3. The method of claim 1, wherein the propensity metric obtained at step (a) is indicative of the patient's propensity for the first disorder.

4. The method of claim 1, wherein the propensity metric obtained at step (a) is indicative of the patient's propensity for the second disorder.

5. The method of claim 1, wherein:
   step (a) includes obtaining a first propensity metric indicative of the patient propensity for the first disorder, and obtaining a second propensity metric indicative of the patient's propensity for the second disorder that is also known to affect T-wave morphology; and
   step (d) includes taking into account the patient's propensity for the first disorder, the patient's propensity for the second disorder and the T-wave variability, when determining the diagnosis for detecting the specific change in T-wave morphology.

6. The method of claim 1, wherein the first disorder is one of the following:
   diabetes;
   myocardial ischemia;
   kidney disfunction; and
   coronary artery disease.

7. The method of claim 6, wherein the propensity metric obtained at step (a) is indicative of the patient's propensity for the first disorder.

8. The method of claim 6, wherein the propensity metric obtained at step (a) is indicative of the patient's propensity for the second disorder that is also known to affect T-wave morphology; and the second disorder is one of the following, but different than the first disorder:
   diabetes;
   myocardial ischemia;
   kidney disfunction; and
   coronary artery disease.

9. The method of claim 1, wherein the first disorder is diabetes, and the episodes relating to the first disorder are hypoglycemic episodes or hyperglycemic episodes.

10. The method of claim 1, wherein the first disorder is myocardial ischemia, and the episodes relating to the first disorder are ischemic episodes.

11. The method of claim 1, wherein the first disorder is kidney disfunction, and the episodes relating the disorder are hyperkalemic episodes or hypokalemic episodes.

12. The method of claim 1, wherein the first disorder is coronary artery disease, and the episodes relating to the first disorder are episodes of angina.

13. The method of claim 1, wherein step (b) comprises:
   (b.1) measuring one or more T-wave metric of T-waves in one or more IEGM and/or ECG obtained for the patient; and
   (b.2) determining the T-wave variability based on the measured T-wave metrics.

14. The method of claim 13, wherein the one or more T-wave metric, upon which T-wave variability is based, comprises one or more of the following:
   peak-to-peak amplitude of T-wave;
   maximum amplitude of T-wave;
   location of maximum amplitude of T-wave;
   minimum amplitude of T-wave;
   location of minimum amplitude of T-wave:
   area under T-wave;
   slope of T-wave;
   T-wave centroid;
   QT interval;
   corrected QT interval;
   amplitude of ST segment;
   QT max-QT end;
   T-wave frequency content; and
   T-wave frequency spread.

15. A system for diagnosing, with improved specificity, occurrences of episodes relating to a first disorder that is known to affect T-wave morphology, the system comprising:
   memory to store a propensity metric indicative of a patient's propensity for a specific disorder, where the specific disorder is either the first disorder or a second disorder that is also known to affect T-wave morphology;
   a T-wave monitor to monitor T-wave variability and to monitor for a specific change in T-wave morphology that is known to be indicative of episodes relating to the first disorder; and
   a disorder detector to determine a diagnosis for detection of the specific change in T-wave morphology, wherein the disorder detector takes into account the propensity metric and the T-wave variability when determining the diagnosis.

16. The system of claim 15, wherein the disorder detector determines a level of confidence corresponding to the diagnosis.

17. The system of claim 15, wherein the propensity metric is indicative of the patient's propensity for the first disorder.

18. The system of claim 15, wherein the propensity metric is indicative of the patient's propensity for the second disorder.

19. The system of claim 15, wherein:
   the memory stores a first propensity metric indicative of the patient's propensity for the first disorder;
   the memory stores a second propensity metric indicative of the patient's propensity for the second disorder that is also known to affect T-wave morphology; and
   the disorder detector takes into account T-wave variability, the patient's propensity for the first disorder, and the patient's propensity for the second disorder, when a diagnosis is determined for detection of the specific change in T-wave morphology.

20. A method for diagnosing, with improved specificity, occurrences of episodes of disorders that are known to affect T-wave morphology, the method comprising:

(a) obtaining propensity metrics, each of which are indicative of a patient's propensity for a specific disorder that is known to affect T-wave morphology;

(b) monitoring for a specific change in T-wave morphology;

(c) monitoring T-wave variability; and (d) using a microprocessor to determine a diagnosis, taking into account T-wave morphology, T-wave variability and at least one of the propensity metrics.

21. The method of claim 20, wherein step (d) includes taking into account a plurality of the propensity metrics.

* * * * *